United States Patent
Jensen et al.

(10) Patent No.: US 10,166,149 B2
(45) Date of Patent: Jan. 1, 2019

(54) HARDENING INITIATION LAMP AND USE THEREOF

(71) Applicant: Straxfix.Technology IVS, Hellerup (DK)

(72) Inventors: Torben Hove Jensen, Højbjerg (DK); Lars Carl Borris, Aarhus C (DK)

(73) Assignee: STRAXFIX.TECHNOLOGY IVS (DK)

( * ) Notice: Subject to any disclaimer, the term of this patent is extended or adjusted under 35 U.S.C. 154(b) by 124 days.

(21) Appl. No.: 14/904,591

(22) PCT Filed: Jul. 11, 2014

(86) PCT No.: PCT/DK2014/050219
§ 371 (c)(1),
(2) Date: Jan. 12, 2016

(87) PCT Pub. No.: WO2015/003724
PCT Pub. Date: Jan. 15, 2015

(65) Prior Publication Data
US 2016/0151210 A1    Jun. 2, 2016

(30) Foreign Application Priority Data

Jul. 12, 2014    (DK) ................................ 2013 70401

(51) Int. Cl.
*F21V 1/00* (2006.01)
*A61F 13/04* (2006.01)
(Continued)

(52) U.S. Cl.
CPC .............. *A61F 13/041* (2013.01); *F21K 9/60* (2016.08); *F21V 9/00* (2013.01); *F21V 9/06* (2013.01);
(Continued)

(58) Field of Classification Search
CPC . A61F 13/041; F21K 9/60; F21V 9/00; F21V 9/06; F21W 2131/20; F21Y 2103/37; F21Y 2115/10
(Continued)

(56) References Cited

U.S. PATENT DOCUMENTS 3,874,376 A    4/1975    Dart
3,930,320 A *  1/1976    Henderson ............. A45D 29/18
                                                34/202

(Continued)

FOREIGN PATENT DOCUMENTS

FR    2782468 A1    2/2000
JP    2000065999 A    3/2000
(Continued)

OTHER PUBLICATIONS

International Search Report for corresponding application PCT/DK2014/050219 filed Jul. 14, 2014; dated Oct. 28, 2014.
(Continued)

*Primary Examiner* — Tsion Tumebo
(74) *Attorney, Agent, or Firm* — Sean D. Detweiler, Esq.; Morse, Barnes-Brown & Pendleton, P.C.

(57) ABSTRACT

A hardening initiation lamp for illumination of a light-hardenable bandage, where the lamp is shaped so that it can at least partially enclose the bandage, the lamp including an inner side, which is substantially arranged to face inwards towards the bandage when the latter is illuminated, and an outer side, which is substantially arranged to face away from the bandage when the latter is illuminated, the lamp further including at least one hardening light source having means to initiate a hardening process in the bandage, and at least one illumination light source, which can emit light in the visible spectrum, arranged to illuminate the bandage at least while the hardening process is initiated in the bandage, both (Continued)

the hardening light source and the illumination light source being arranged to emit light from the inner side, substantially in the direction of the bandage, and the lamp further including one or more observation areas, where a light filter is arranged, which allows light from the illumination light source to pass through the lamp from the inner side and out through the outer side.

19 Claims, 3 Drawing Sheets

(51) Int. Cl.
*F21V 9/00* (2018.01)
*F21V 9/06* (2018.01)
*F21K 9/60* (2016.01)
*F21W 131/20* (2006.01)
*F21Y 103/37* (2016.01)
*F21Y 115/10* (2016.01)

(52) U.S. Cl.
CPC ...... *F21W 2131/20* (2013.01); *F21Y 2103/37* (2016.08); *F21Y 2115/10* (2016.08)

(58) Field of Classification Search
USPC .......................................................... 362/235
See application file for complete search history.

(56) References Cited

U.S. PATENT DOCUMENTS

| | | | |
|---|---|---|---|
| 7,328,708 B2* | 2/2008 | Malak | A61N 5/0616 128/898 |
| 9,713,371 B1* | 7/2017 | Luu | A45D 29/00 |
| 2004/0149936 A1 | 8/2004 | Schweitzer | |
| 2008/0199354 A1* | 8/2008 | Gordon | A61L 2/10 422/24 |
| 2009/0160923 A1* | 6/2009 | Custer | B41F 23/0453 347/102 |
| 2009/0273936 A1 | 11/2009 | Wakalopulos | |
| 2010/0220472 A1* | 9/2010 | Dahm | A61C 19/004 362/231 |
| 2011/0277338 A1* | 11/2011 | Li | F26B 3/28 34/275 |
| 2012/0060757 A1* | 3/2012 | Li | F26B 3/28 118/620 |
| 2012/0187311 A1* | 7/2012 | Vu | A45D 29/00 250/492.1 |

FOREIGN PATENT DOCUMENTS

| | | |
|---|---|---|
| JP | 2008221170 A | 9/2008 |
| WO | 2010017817 A2 | 2/2010 |

OTHER PUBLICATIONS

Written Opinion for corresponding application PCT/DK2014/050219 filed Jul. 14, 2014; dated Oct. 28, 2014.

* cited by examiner

HARDENING INITIATION LAMP AND USE THEREOF

TECHNICAL FIELD

The present invention relates to a hardening initiation lamp for illumination of a light-hardenable bandage, the lamp being shaped in such a way as to at least partially enclose the bandage. The lamp comprises an inner side, which is substantially arranged to face inwards towards the bandage when the latter is illuminated, and an outer side, which is substantially arranged to face away from the bandage when the latter is illuminated. The lamp furthermore comprises a hardening light source comprising means to initiate a hardening process in the bandage. The invention furthermore relates to use thereof.

BACKGROUND

It is known to produce bandages comprising means enabling the hardening process of the bandage to be initiated using light—typically light at specific wavelengths. However, to initiate the hardening uniformly and efficiently, the bandage must typically be exposed to light of considerable intensity, which can be harmful to the skin and/or eyes of an observer.

From international patent application WO 2010/017817 A2 it is therefore known to design a hardening initiation lamp as an arched lamp that can be placed around a bandage applied to an arm, for example. Thereby, only limited amounts of light are emitted to the surroundings, but the enclosing form also means that the bandage and especially the location of the bandage cannot be observed properly while the lamp is positioned and during the subsequent illumination.

It is therefore an object of the invention to provide a hardening initiation lamp enabling improved control of the bandage while at the same time reducing the risk of an observer being harmed by light from the light source which is to initiate the hardening process in a bandage.

BRIEF SUMMARY

The invention relates to a hardening initiation lamp for illumination of a light-hardenable bandage, where the lamp is shaped in such a way that it can at least partially enclose the bandage. The lamp comprises an inner side, which is substantially arranged to face inwards towards the bandage when the latter is illuminated, and an outer side, which is substantially arranged to face away from the bandage when the latter is illuminated. The lamp furthermore comprises at least one hardening light source comprising means to initiate a hardening process in the bandage, and at least one illumination light source emitting light in the visible spectrum, arranged to illuminate said bandage at least while said hardening process is initiated in the bandage, wherein both the hardening light source and the illumination light source are arranged to emit light from the inner side, substantially in the direction of the bandage. The lamp also comprises one or more observation areas wherein a light filter is arranged, which allows light from the illumination light source to pass through the lamp from the inner side and out through the outer side.

For the sake of clarity, the singular forms "(the) hardening light source", "(the) illumination light source" and "(the) observation area" are most often used in the following, but it should still be understood that the lamp may comprise more than one of one or more of these elements, as mentioned above.

It is advantageous to provide a hardening initiation lamp with an illumination light source, as it is hereby possible to illuminate the bandage, even if the hardening light source is shut off or emits light at wavelengths outside the visible spectrum. In addition, it is advantageous to provide the lamp with transparent observation areas so that the bandage may be observed through the observation areas—even while the hardening light source is on—and it is advantageous to provide this or these observation areas with a light filter, through which an observer can see whatever is illuminated by the illumination light source, while the light filter simultaneously ensures against the observer being harmed by light from the hardening light source.

Since the unhardened bandage is very soft, it is important that the hardening initiation lamp does not touch the bandage while the lamp is being placed above it or in connection with initiation of the hardening, and it is therefore especially advantageous that you are able to look through the hardening initiation lamp when this is to be placed above the bandage as well as during the hardening initiation itself.

It should be pointed out that the sentence "arranged to illuminate said bandage at least while said hardening process is initiated" means that the illumination light source can at the least emit light while the hardening process is initiated, but it is not limited to mean that the illumination light source must emit light during the entire hardening initiation process.

One aspect of the invention is that said light filter comprises means to attenuate light emitted by said hardening light source.

The hardening light source will typically emit powerful light at specific wavelengths, which light can be harmful to the patient or an observer. It is therefore advantageous to let the light filter comprise means to attenuate light from the hardening light source.

It should be pointed out that the term "attenuate" in this context should be taken to mean that the light filter can reduce the intensity of light emitted by the hardening light source, e.g. by the light filter partially absorbing or reflecting light at specific or all wavelengths.

One aspect of the invention is that said light filter comprises means to block or attenuate light with specific wavelengths emitted by said hardening light source.

It is advantageous to provide the light filter with means to block or attenuate light with specific wavelengths rather than aiming for the same effect on all wavelengths, as it can hereby most easily be ensured that you can see through the light filter while the observer is simultaneously protected against being harmed by light from the hardening light source.

One aspect of the invention is that said light filter can attenuate or completely prevent passage of light with at least a wavelength between 100 and 600 nm, preferably between 150 and 500 nm and most preferably between 200 and 450 nm.

Powerful light at especially these wavelengths can harm both the eyes and the skin, and it is therefore especially important that the light filter attenuates light in these wavelength ranges.

In another embodiment, the light filter could be adapted to also or instead attenuate or completely prevent passage of light with at least a wavelength between 100 and 750 nm, between 150 and 600 nm, between 200 and 550 nm, between 220 and 500 nm or between 250 and 450 nm.

However, it is important to point out that this should not be taken to mean that the light filter exclusively comprises means to block or attenuate light with wavelengths within one or more of these intervals or that all light emitted by the hardening light source is exclusively within one or more of these intervals, for that matter. The light filter will typically have different attenuation levels for different wavelengths. There will therefore typically be no sharp delimitation for the effective range of the light filter, and likewise, the hardening light source will typically emit light at many different wavelengths. The foregoing should therefore be understood so that the light filter is at least able to block or attenuate light at given wavelengths, and likewise it should be understood that light emitted by the hardening light source will typically cover a relatively wide spectrum, but that most light will be emitted in said intervals, and/or that the light in these intervals is the most powerful.

One aspect of the invention is that said one or more observation areas cover between 5 and 100%, preferably between 20 and 90%, and most preferably between 40 and 85% of said outer side of said hardening initiation lamp.

If the observation area(s) cover too much of the lamp, it may be difficult to make the lamp structurally stable, and it may be difficult to provide it with desired components and properties. However, if the observation area covers too little of the lamp, it may be difficult to observe the bandage during operation. Said area intervals are therefore expressions of an advantageous correspondence between design and function.

One aspect of the invention is that said hardening initiation lamp comprises at least an elongate lamp part, where a cross-section of said elongate lamp part is substantially horse shoe-shaped.

It is advantageous to shape the lamp part with a horse shoe-shaped cross-section, as this form enables maintaining a relatively uniform distance from the inner side of the lamp to the bandage.

It should be pointed out that the term "horse shoe-shaped" in this context should be taken to mean that a cross-section of the lamp is shaped like an arc section, as a semi-circle, as a U, as part of a polygon or as any combination thereof, or has been given any other form with some resemblance to a horse shoe, so that the lamp at this cross-section can at least partially enclose a bandage placed on e.g. a forearm, a shin, a wrist or something else.

One aspect of the invention is that said hardening light source comprises a plurality of light-emitting diodes.

Compared to other light sources, light-emitting diodes have great reliability and very long life, and they also display a favorable relationship between, on the one hand, light yield and, on the other hand, weight, space requirements and price. Since these advantages are very desirable in a hardening initiation lamp, among other things because it must be continually handled, the use of light-emitting diodes in such a lamp is especially advantageous.

One aspect of the invention is that said means to initiate a hardening process in said bandage comprises means to emit light with a power density of between 20 and 5000 $W/m^2$, preferably between 100 and 3000 $W/m^2$ and most preferably between 200 and 1500 $W/m^2$ measured as an average at said inner side.

If the power density of the hardening initiation light is too low, the chemical reactions in the bandage material may not proceed in the desired way, and the bandage will typically be underhardened, i.e. not obtain the required strength. However, if the power density is too high, the energy consumption will become too great, and the risk of damage from the light is increased. The above-mentioned intervals therefore represent an advantageous correspondence between power density and function.

In another embodiment, the means to initiate a hardening process in the bandage could also or instead comprise means to emit light with a power density of between 50 and 4000 $W/m^2$, preferably between 150 and 2000 $W/m^2$, such as 1000 $W/m^2$.

One aspect of the invention is that said hardening initiation lamp comprises an integrated operating panel for manual actuation of said hardening light source and/or said illumination light source.

Since the hardening light source and the illumination light source can be relatively energy consuming, it is advantageous that these can easily be turned on and off directly on the lamp.

One aspect of the invention is that said hardening initiation lamp comprises one or more object sensors arranged to detect whether said inner side and/or a bottom edge of said hardening initiation lamp is in the proximity of another object.

Hereby, an advantageous embodiment of the invention is obtained, as the sensors may form part of a safety function as described below.

It should be noted that for a lamp with a substantially horse shoe-shaped cross-section, "bottom edge" must typically be understood as an edge running parallel to the longitudinal axis of the lamp and perpendicular to one of the legs of the horse shoe, such an edge typically forming a lower limitation of the lamp when the latter is positioned in its usual position for hardening of a bandage.

One aspect of the invention is that said hardening initiation lamp comprises control means arranged so that said hardening light source can only be actuated if said one or more object sensors detect an object.

Since the light from the hardening light source may be dangerous to the skin and eyes of an observer, it is advantageous to provide the hardening initiation lamp with one or more object sensors which can ensure that the hardening light source cannot be actuated until the hardening initiation lamp has been positioned around an object—such as an arm with a bandage—or when it is positioned on an object—such as a table—with the hardening light source pointing downwards.

One aspect of the invention is that said hardening light source and said illumination light source are supplied by the same energy source and that this energy source is placed in or on said hardening initiation lamp.

It is advantageous to supply both the hardening light source and the illumination light source from the same energy source, as this reduces costs and simplifies the design. It is also advantageous to position this energy source on the hardening initiation lamp, as this enables the hardening initiation lamp to function in a wire-free manner, i.e. without having to be connected to external, electrical wires under illumination of a bandage, which will increase the usability and user-friendliness.

One aspect of the invention is that said illumination light source can be switched on and off independently from said hardening light source.

It is advantageous that the illumination light source and the hardening light source can be turned on independently from each other, as this makes it possible to only turn on the light source required in a given situation. You can thus settle for having the illumination light source on during the preparations for the hardening without initiating it.

One aspect of the invention is that said hardening light source is arranged separately from said illumination light source.

It is advantageous to arrange the hardening light source and the illumination light source as separate units, as this makes it possible for them to be turned on and replaced separately.

One aspect of the invention is that said hardening light source and said illumination light source are integrated in the same light source.

It is advantageous to integrate the hardening light source and the illumination light source in the same light source, this being space-saving and cost-efficient, as the total number of light sources can be reduced.

One aspect of the invention is that said light filter comprises means to attenuate light of at least one wavelength emitted by said hardening light source by at least 10%, preferably by at least 30% and most preferably by at least 50%.

It is cumbersome and costly to attenuate all light at a specific wavelength while at the same time ensuring that you can observe the bandage through the light filter. However, you must ensure that the light filter effectively attenuates light with a potentially harmful wavelength. The above-mentioned attenuation limits are therefore an expression of an advantageous correspondence between price and functionality.

The invention furthermore relates to use of a hardening initiation lamp according to the previously described hardening initiation lamps to initiate the hardening of a light-hardenable bandage.

BRIEF DESCRIPTION OF THE DRAWINGS

The invention is explained in the following with reference to drawings, where.

DETAILED DESCRIPTION

Figure 1:
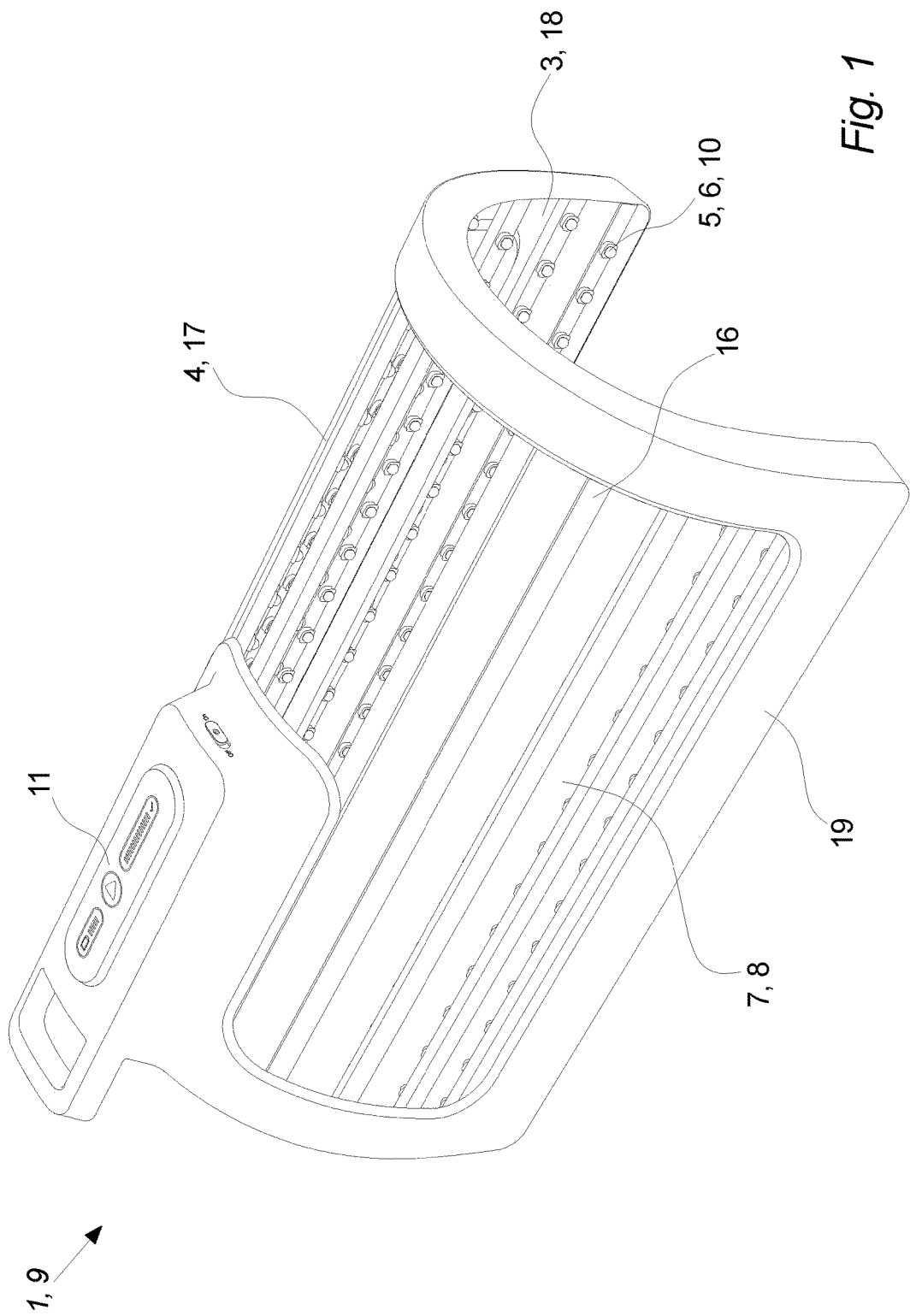
FIG. 1 shows a perspective view of a hardening initiation lamp.

FIG. 1 shows a perspective view of a hardening initiation lamp 1.

In this embodiment, the cross-section of the hardening initiation lamp 1 is substantially horse shoe-shaped, the lamp cross-section being shaped as a semi-circle which at both ends is elongated by legs that extend linearly. However, in another embodiment the horse shoe shape could be realized differently. For example, the "legs" could be shorter or longer, the arc could be shaped as something other than a circle section—such as a polygon section or ellipsis section—or be shaped as a more or less complex curve or any combination thereof, or the hardening initiation lamp 1 could be made to partially enclose the bandage 2 in some other way e.g. by a V-shape, a semi-circle, a tube or something else.

In this embodiment, the lamp is approx. 380 mm long and the arc is shaped with an inner radius of approx. 110 mm, so that the lamp is suited for enclosing an arm, a wrist or a shin of an adult person. However, in another embodiment the lamp 1 could obviously have other dimensions—such as 100 mm long, 200 mm long, 300 mm long, 500 mm long, 600 mm long or longer, and the inside maximum width could be 50 mm, 80 mm, 140 mm, 200 mm or more—e.g. adapted to the current use. So if the lamp was to be used to harden a bandage around a thigh of an adult man, it would probably have to be larger, whereas it could be smaller if it was to be used to harden the bandage on the forearm of a small child. However, it should be mentioned that the use of the hardening initiation lamp 1 is no way limited to initiating the hardening of bandages on humans. The hardening initiation lamp 1 may just as well be used in connection with animals, plants and others.

In this embodiment, the hardening initiation lamp 1 is shaped as a simple gutter piece with a constant cross-section, but in another embodiment of the invention, the hardening initiation lamp 1 could e.g. be designed with a bend so that it could be arranged around a bent elbow joint or knee joint, and/or the cross-section could vary in the longitudinal direction of the hardening initiation lamp 1, e.g. to adjust it better to the shape of a forearm or a leg.

In another embodiment, the hardening initiation lamp 1 could be designed with a bottom part—e.g. in the form of a bottom plate that was hinged to a main lamp part—e.g. a part equal to the one shown in FIGS. 1-4—so that the injured body part with bandage 2 would have to be positioned on the bottom part, whereafter the main lamp part was tilted down over the bandage 2. In such an embodiment, the bottom part could also be provided with hardening light sources 5 and/or illumination light sources 6, and/or the bottom part could comprise power supply to the light sources 5, 6, and it could comprise sensors, safety switches and others. Or it could comprise a system for cooling of the light sources 5, 6, e.g. by actively circulating air or coolant past or through them.

In the embodiment shown in FIG. 1, the hardening initiation lamp 1 is provided with a plurality of hardening light sources 5 in the form of light-emitting diodes positioned on printed circuits attached to rods 16 arranged in the longitudinal direction of the lamp 1. In other embodiments, the hardening light sources 5 could be arranged individually, they could be arranged in groups, or the lamp 1 could comprise exactly one hardening light source 5, and/or these could be attached in another way, e.g. directly on a printed circuit board, cast into the lamp shell material or otherwise, or the rods 16 could be arranged differently, such as in arched rods 16 extending across the longitudinal direction of the lamp.

In this embodiment, all the light sources 5, 6 are arranged so that they shine inwards towards a bandage 2 (not shown) positioned under the lamp 1. The light sources 5, 6 are thus arranged to emit light from the inner side 3 of the lamp 1 in the direction of the bandage 2.

In this embodiment, the lamp 1 contains two-hundred-and-ten hardening light sources 5, the lamp 1 containing fourteen rods 16 of each fifteen hardening light sources 5. Obviously, the number of hardening light sources 5 is given by the power of the individual hardening light sources 5, of the total area of the lamp 1, of the amount of light required to initiate the hardening of a specific bandage type etc., and it is therefore obvious that the number of hardening light sources 5 can be varied and adjusted almost infinitely.

In this embodiment, the rods 16 are preferably made from aluminum and serve to absorb and distribute heat from the hardening light sources 5 during illumination. In another embodiment, the rods 16 could be made from a different material with a high thermal conductivity and a high heat capacity, such as a different metal, e.g. silver, gold, brass, steel or an alloy, or they could be made from a composite material, a plastic material or any combination thereof.

In this embodiment, the lamp 1 is designed with an observation area 7 in the form of a transparent outer shell 17 and a transparent inner shell 18, arranged on an opaque structural part 19, so that an observer can look through the lamp 1 in this observation area 7. In another embodiment, the lamp 1 could comprise several observation areas 7, and the observation area(s) could be limited to comprising either an outer shell 17 or an inner shell 18, and/or they could comprise shells arranged differently, or the observation area 7 could be made from one solid, transparent shell.

In this embodiment, the opaque structural part 19 covers around 10% of the total area of the lamp, meaning that the observation area 7 in this case covers around 90% of the outer side 4 of the lamp. In another embodiment, the observation areas 7 could be limited to covering selected areas of the lamp 1, and the total area of the observation area 7 would therefore be smaller, or the lamp 1 could be shaped with a smaller or no structural part 19, so that the total area of the observation area 7 would be larger or even substantially capable of covering the entire area of the lamp.

The observation area 7 is provided with a light filter 8, which blocks, absorbs or reflects a part of the optical radiation that falls inwards towards the observation area 7, so that the user and the patient are spared from harmful light from the light sources 5, 6. In this particular embodiment, this light filter 8 is created by the outer shell 17, while being transparent, having a color meaning that light at specific wavelengths (substantially corresponding to the wavelength of other colors) will be attenuated or even completely blocked during passage through the light filter 8. For example, the outer shell 17 could have a yellow color so that primarily yellow light would be able to pass through the light filter 8, thus allowing the bandage 2 to be seen through the light filter 8, whereas e.g. harmful light in the ultraviolet, violet and blue ranges would be considerably attenuated during passage through the light filter 8.

It is advantageous that the light filter 8 is arranged in or at the outer shell 17, as the former would thus have no influence on light emitted from the light sources 5, 6 inwards towards the bandage 2, but would only attenuate light with the opposite direction, i.e. out through the lamp 1. However, it is imaginable in another embodiment that it could be advantageous to arrange at least a part of the light filter 8 in or at the inner shell 18.

In another embodiment, parts of or the entire light-attenuating effect of the light filter could be achieved by mirror effect, so that light at all or specific wavelengths was attenuated by the light being reflected by the light filter 8.

In the embodiment shown in FIG. 1, the entire lamp 1 is shaped as a rigid shell, but in another embodiment, one or more parts of the lamp 1 could be hinged in relation to the rest of the lamp 1, or parts of or the entire lamp 1 could be designed flexibly so that it could be better adjusted to the current use.

In this embodiment, the hardening initiation lamp 1 is furthermore provided with an operating panel 11, which can be positioned on top of the lamp 1.

The operating panel 11 can be provided with a button for turning on the hardening light source 5, an on/off button as well as a power indicator. However, it is obvious that the operating panel 11 can be equipped in many different ways and with many different features and functions, and that this can be arranged differently on or outside the lamp 1. For example, the operating panel 11 and/or an underlying control could comprise a timer, which could turn off the lamp 1 after a predefined time period, where this time period could be settable on the operating panel 11. In another embodiment, the lamp could instead or also be remote controlled, so that it could be turned on and/or off via a wireless remote control. This could be advantageous, as you could thereby actuate the lamp 1 without touching it and thus risk displacing it in relation to the bandage.

Figure 3:
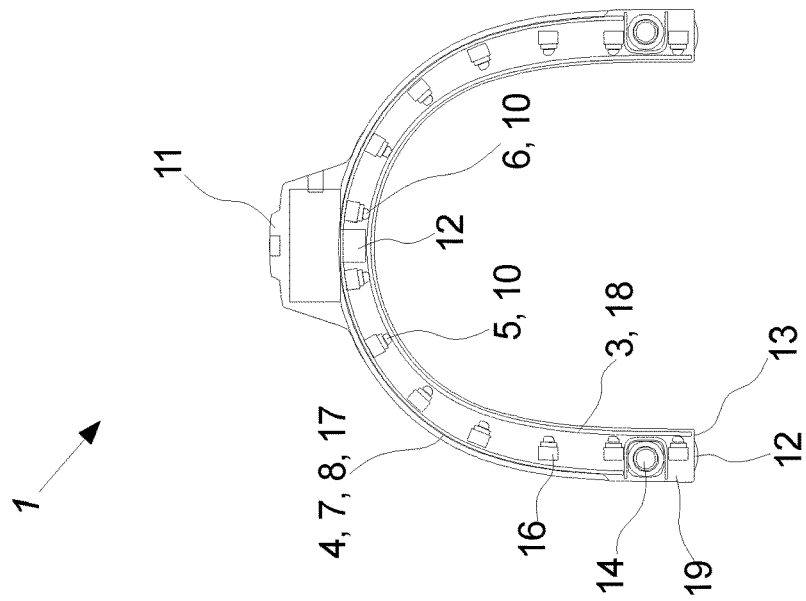
FIG. 3 shows a cross-section of an end view of a hardening initiation lamp.
Figure 2:
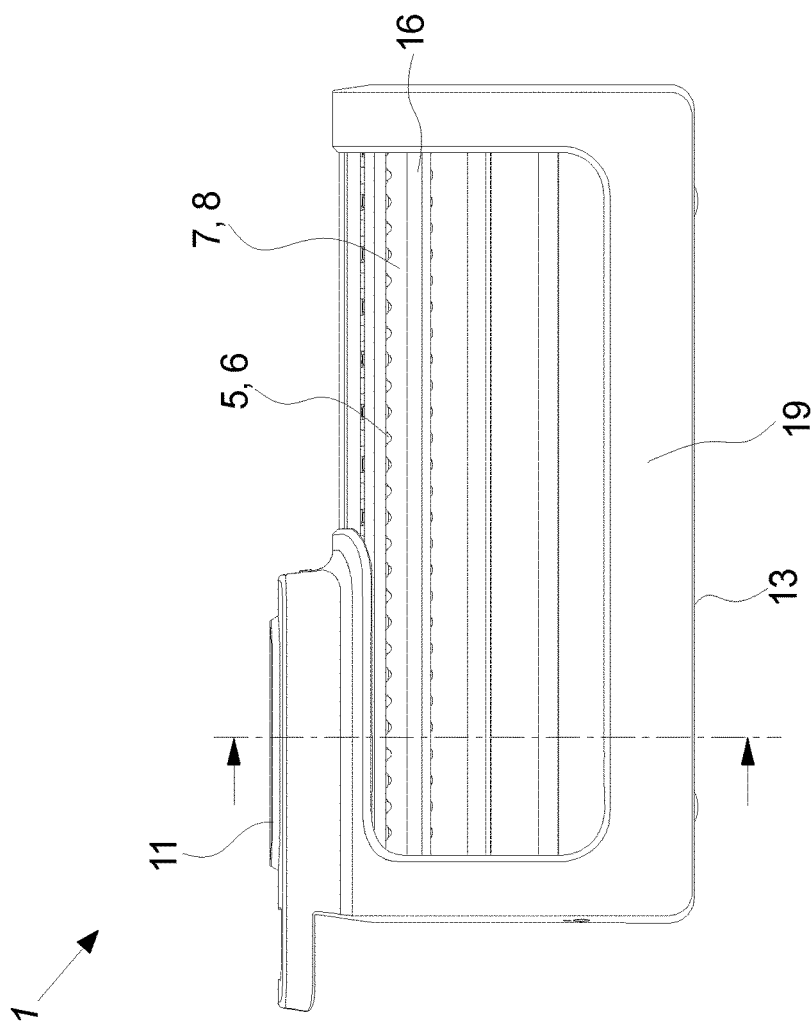
FIG. 2 shows a side view of a hardening initiation lamp.

FIG. 2 shows a side view of a hardening initiation lamp 1, and FIG. 3 shows an end view of a cross-section of this hardening initiation lamp 1.

In this embodiment, the hardening light source 5 and the illumination light source 6 are both supplied with power from the same energy source 14 in the form of rechargeable batteries, which in this embodiment are arranged along the edges of the lamp, so that the hardening initiation lamp 1 is particularly mobile, as it can function wirelessly, i.e. without having to be connected to external, electrical wires during illumination of a bandage. In another embodiment, the hardening light source 5 and the illumination light source 6 could be supplied from separate energy sources 14, and/or the energy source(s) 14 could be arranged externally in relation to the lamp 1. In another embodiment, the energy source(s) 14 could be arranged somewhere else on the lamp 1. Charging of the built-in energy sources 14 could e.g. take place by connection to an external charger through a plug connection when the lamp 1 is not in use.

As the voltage over each light source 5, 6 must typically be within a narrow region, in this embodiment of the invention an electric power converter has been interposed between the energy source 14 and light source 5, 6, whereby the energy source 14 and the light sources 5, 6 can be combined relatively freely in relation to each other, as long as the energy source 14 can deliver the required power.

In this embodiment, the lamp 1 furthermore contains a programmable signal collection and control unit (not shown) arranged at the operating panel 11, which unit is designed for metering the illumination time as well as for signal processing in connection with the safety functions of the lamp 1. The unit can thus be arranged to receive signals from temperature sensors (not shown) placed at or on one or more of the light sources 5, 6 and not allow actuation of the lamp 1 until the temperature is below a set limit. Furthermore, the power consumption can be closely measured during illumination, as a value thereof deviating from a standard value can be a sign of error, e.g. defective light sources 5, 6. Photo sensors (not shown) built into the lamp 1 may serve for regular control of the light intensity, as signals from these photo sensors are processed in the control unit. The control unit can also be used for collection of data on the operation of the lamp. These data can be used to adjust the operating parameters of the lamp as well as in connection with ongoing product development. Error states can be indicated with light or sound signals. The light sources 5, 6 are turned on in this embodiment by pressing a button built into the operating panel 11. Programming with setting of the electrical parameters of the lamp as well as transfer of data from the lamp 1 can e.g. take place wirelessly, possibly using the internet.

In this embodiment, the hardening initiation lamp 1 furthermore comprises an illumination light source 6 in the form of a single light-emitting diode, which predominantly emits visible light, i.e. optical radiation with a wavelength between 380 and 780 nm, so that the bandage 2 (see FIG. 4) can be illuminated while the hardening initiation lamp 1 is installed and removed, and/or while the hardening light sources 5 are active.

In another embodiment, the hardening light source 5 and/or the illumination light source 6 could be another form of light source, such as a light source comprising a filament, electroluminescent band, plate or wire or other forms of light sources or combinations of light sources suited for use in a hardening initiation lamp 1.

In the embodiment shown in FIG. 2, each of the two-hundred-and-ten hardening light sources 5 have a power of approx. 0.3 W, understood as emitted light output, and as the total area of the inner side 3 of the lamp is approx. 0.07 m$^2$, the inner side 3 of the hardening initiation lamp 1 in this case has an average power density of around 900 W/m$^2$. And it is important to emphasize that this is an average, as it is obvious that the power density locally can be larger or smaller, depending on the design and use of the lamp and on the location of the hardening light sources 5.

In this embodiment, this one illumination light source 6 is arranged as one of the many light sources on the rods 16, but in another embodiment, the illumination light source 6 could be arranged in the lamp 1 in a different way than the hardening light sources 5, and/or the lamp 1 could be provided with several illumination light sources 6, e.g. arranged to illuminate a bandage from several angles, and/or the illumination light sources 6 could be integrated in the hardening light sources 5, so that the two sets of light sources could only light simultaneously. If the illumination light sources 6 and the hardening light sources 5 were in practice the same light sources, then each of these light sources 5, 6 should be able to both emit optical radiation with a wavelength that could initiate the hardening process in the bandage 2 (see FIG. 4), and light with a wavelength that would illuminate the bandage 2, so that the latter and the process could be monitored through the observation area 7. In such a case, the hardening initiation light could be in a non-visible range, e.g. in an ultraviolet range and/or in a visible violet or blue range, e.g. with a wavelength of between 100 and 450 nm, which is not necessarily a light range that is suited for illuminating the bandage so that the latter and the process could be monitored through the observation area 7, whereas the illumination light emitted from the same light source could have wavelengths that were in the remaining visible spectrum, e.g. between 450 and 700 nm, so that the bandage was properly illuminated, and so that it was possible to adapt the light filter 8 in such a way that primarily the harmful hardening initiation light was attenuated. In another embodiment where the illumination light sources 6 and the hardening light sources 5 were in practice the same light source, it was also imaginable that the hardening initiation light had wavelengths in the visible range, so that the hardening initiation light and the illumination light would be exactly the same light, which would thus simultaneously initiate the hardening in the bandage and illuminate the bandage, and which would be attenuated by the light filter during passage through the latter, so that you could look through the observation areas 7 during the hardening process without being harmed by optical radiation from the light sources 5, 6.

In this embodiment, the hardening initiation lamp 1 is furthermore provided with object sensors 12 in the form of distance sensors built into the edges 13 of the lamp to detect whether the lamp 1 is positioned against a base. In another embodiment, these object sensors 12 in the bottom edge 13 of the lamp could be supplemented or replaced by one or more object sensors 12 arranged at the inner side 3 of the lamp 1, so that a bandage 2 or similar placed under the lamp 1 could be detected. These object sensors 12 would then have to be connected to control means, e.g. in the form of the previously mentioned control unit, so that the lamp 1 could only be turned on if the object sensors 12 detected that the lamp 1 was positioned against a base, and/or that an object was placed inside the lamp 1, whereby the danger of unintended light impact on eyes and skin would be reduced.

Figure 4:
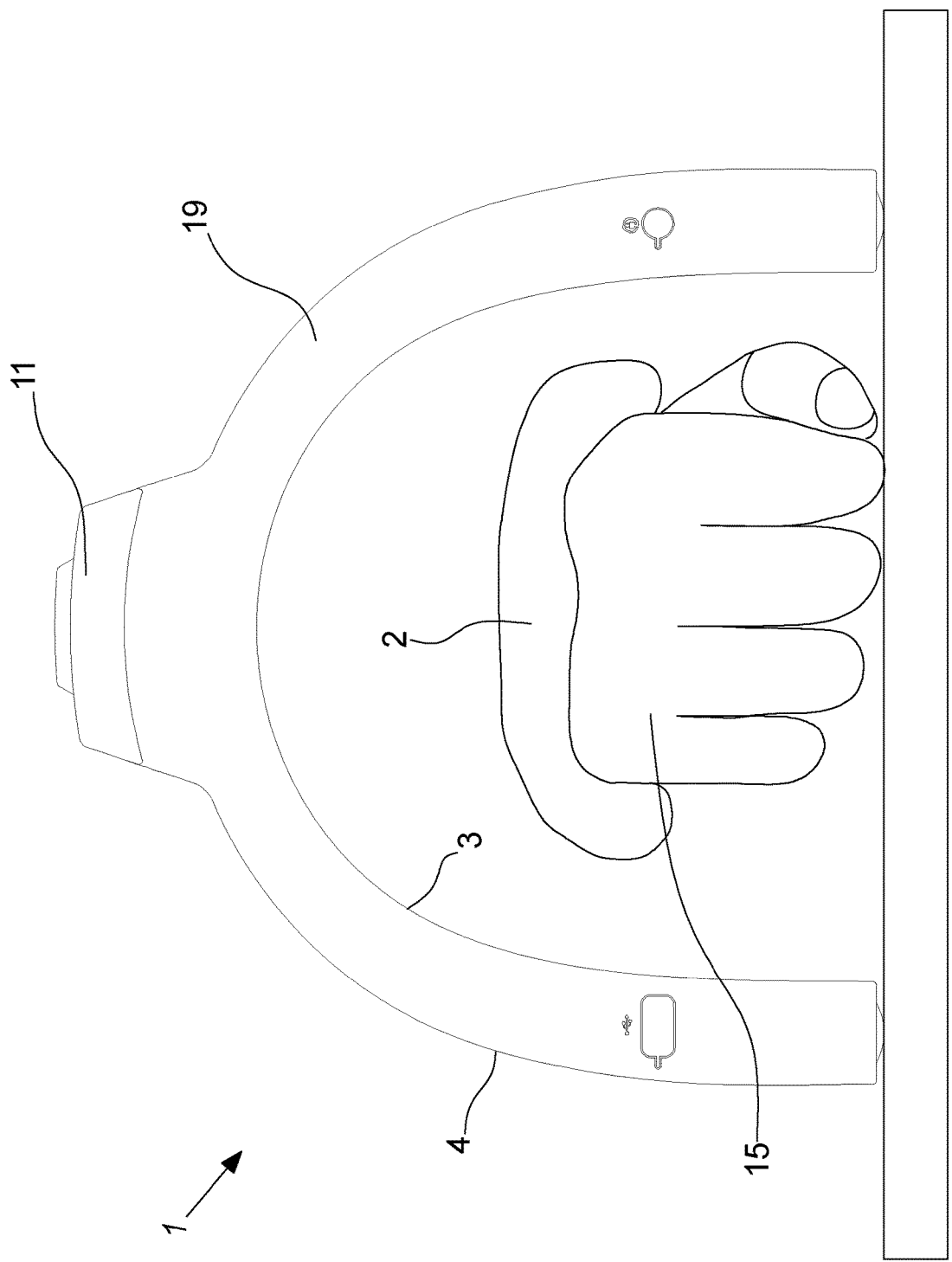
FIG. 4 shows an end view of a hardening initiation lamp which partially encloses an arm with a bandage.

FIG. 4 shows and end view of a hardening initiation lamp 1 which partially encloses an arm 15 with a bandage 2.

In this embodiment, the hardening initiation lamp 1 functions as follows. Firstly, the bandage 2 is laid on the injured body part, whereafter the hardening initiation lamp 1 is positioned over the bandage 2. In another embodiment, the injured body part with the bandage 2 could also be placed in a stationary hardening initiation lamp 1. While lamp 1 and bandage 2 etc. were arranged in relation to each other, the illumination light source 6 could be turned on, e.g. to ensure that the lamp 1 did not touch the bandage 2 and that the lamp 1 was positioned relatively symmetrically in relation to the bandage 2. If the hardening light source 5 and the illumination light source 6 are integrated into the same light source, the illumination light source 6 will not be turned on, however, until the hardening light source 5 is turned on. And the actuation takes place when both bandage and lamp are in place, so that the hardening light source 5 illuminates the bandage 2 for a while—typically 30 to 45 seconds—whereafter the lamp 1 is removed again while the bandage 2 completes hardening. In the foregoing, the invention has been described in connection with specific embodiments of hardening initiation lamps 1, hardening light sources 5, illumination light sources 6 and others, such as shown in the drawings, but it will be clear to a person skilled in the art that the invention can be varied in countless ways within the framework of the following claims.

The invention claimed is:

1. A hardening initiation lamp for illumination of a light-hardenable bandage, where said lamp is shaped so that it can at least partially enclose said bandage, where said lamp comprises:
   an inner side, which is substantially arranged to face inwards towards said bandage when the latter is illuminated;
   an outer side, which is substantially arranged to face away from said bandages when the latter is illuminated, and where said lamp furthermore comprises:
   at least one hardening light source comprising means to initiate a hardening process in said bandage; and
   at least one illumination light source, which emits light in the visible spectrum, arranged to illuminate said bandage at least while said hardening process is initiated in said bandage, where both said hardening light source and said illumination light source are arranged to emit light from said inner side substantially in the direction of said bandage, and where said lamp furthermore comprises one or more transparent observation areas, where a light filter is arranged, which allows light from said illumination light source to pass through said lamp from said inner side and out through said outer side;
   wherein the at least one hardening light source and the at least one illumination light source are arranged in a longitudinal direction along the hardening initiation lamp; and
   wherein the one or more observation areas are interspersed between the at least one hardening light source and the at least one illumination light source.

2. A hardening initiation lamp according to claim 1, where said light filter comprises means to attenuate light emitted by said hardening light source.

3. A hardening initiation lamp according to claim 1, where said light filter comprises means to block or attenuate light with specific wavelengths emitted by said hardening light source.

4. A hardening initiation lamp according to claim 1, where said light filter can attenuate or completely prevent passage of light with at least a wavelength between 100 and 600 nm.

5. A hardening initiation lamp according to claim 1, where said one or more observation areas covers between 5 and 100% of said outer side of said hardening initiation lamp.

6. A hardening initiation lamp according to claim 1, where said hardening initiation lamp comprises at least an elongate lamp part, and where a cross-section of said elongate lamp part is substantially horse shoe-shaped.

7. A hardening initiation lamp according to claim 1, where said hardening light source comprises a plurality of light-emitting diodes.

8. A hardening initiation lamp according to claim 1, where said means to initiate a hardening process in said bandage comprises means to emit light with a power density of between 20 and 5000 $W/m^2$ measured as an average at said inner side.

9. A hardening initiation lamp according to claim 1, where said hardening initiation lamp comprises an integrated operating panel for manual actuation of said hardening light source or said illumination light source.

10. A hardening initiation lamp according to claim 1, where said hardening initiation lamp comprises one or more object sensors arranged to detect whether said inner side or a bottom edge of said hardening initiation lamp is in a proximity of another object.

11. A hardening initiation lamp according to claim 10, where said hardening initiation lamp comprises control means arranged so that said hardening light source can only be actuated if said one or more object sensors detect an object.

12. A hardening initiation lamp according to claim 1, where said hardening light source and said illumination light source are supplied by the same energy source, and where this energy source is placed in or on said hardening initiation lamp.

13. A hardening initiation lamp according to claim 1, where said illumination light source can be turned on and off independently of said hardening light source.

14. A hardening initiation lamp according to claim 1, where said hardening light source is arranged separately from said illumination light source.

15. A hardening initiation lamp according to claim 1, where said hardening light source and said illumination light source are integrated in a same light source.

16. A hardening initiation lamp according to claim 1, where said light filter comprises means to attenuate light of at least one wavelength emitted by said hardening light source by at least 10%.

17. A hardening initiation lamp according to claim 1, where said hardening initiation lamp comprises an integrated operating panel for manual actuation of said hardening light source and said illumination light source.

18. A hardening initiation lamp according to claim 1, where said hardening initiation lamp comprises one or more object sensors arranged to detect whether said inner side and a bottom edge of said hardening initiation lamp is in a proximity of another object.

19. A hardening initiation lamp according to claim 1, wherein said at least one hardening light source and said at least one illumination light source comprise a plurality of light emitting diodes (LEDs) attached to rods arranged in a longitudinal direction of said lamp.

\* \* \* \* \*